United States Patent
Kai et al.

(10) Patent No.: US 11,135,425 B2
(45) Date of Patent: Oct. 5, 2021

(54) DEVICE FOR SUPPRESSING INFLAMMATION AND HYPERIMMUNITY, AND METHOD FOR SUPPRESSING INFLAMMATION AND HYPERIMMUNITY

(71) Applicant: NATIONAL UNIVERSITY CORPORATION KUMAMOTO UNIVERSITY, Kumamoto (JP)

(72) Inventors: Hirofumi Kai, Kumamoto (JP); Tsuyoshi Shuto, Kumamoto (JP); Ann Soten Mary Suico, Kumamoto (JP); Eiichi Araki, Kumamoto (JP); Tatsuya Kondo, Kumamoto (JP)

(73) Assignee: NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 361 days.

(21) Appl. No.: 15/768,253

(22) PCT Filed: Oct. 13, 2016

(86) PCT No.: PCT/JP2016/080443
§ 371 (c)(1),
(2) Date: Sep. 17, 2018

(87) PCT Pub. No.: WO2017/065239
PCT Pub. Date: Apr. 20, 2017

(65) Prior Publication Data
US 2019/0022384 A1    Jan. 24, 2019

(30) Foreign Application Priority Data
Oct. 14, 2015    (JP) .............................. JP2015-203033

(51) Int. Cl.
*A61N 1/36*    (2006.01)
*A61N 1/32*    (2006.01)
(Continued)

(52) U.S. Cl.
CPC ........... *A61N 1/3606* (2013.01); *A61N 1/042* (2013.01); *A61N 1/08* (2013.01); *A61N 1/32* (2013.01);
(Continued)

(58) Field of Classification Search
USPC ...................................... 607/2, 44
See application file for complete search history.

(56) References Cited

U.S. PATENT DOCUMENTS

| | | |
|---|---|---|
| 6,535,767 B1 | 3/2003 | Kronberg |
| 2005/0010163 A1 | 1/2005 | Aoki et al. |

(Continued)

FOREIGN PATENT DOCUMENTS

| | | |
|---|---|---|
| JP | 08131560 A | 5/1996 |
| JP | 2008525102 A | 7/2008 |

(Continued)

OTHER PUBLICATIONS

Extended European Search Report dated Jun. 21, 2019 for European patent application No. 16855492.1.
(Continued)

*Primary Examiner* — Nicole F Lavert
(74) *Attorney, Agent, or Firm* — Hunton Andrews Kurth LLP

(57) ABSTRACT

Provided is a new means for suppressing inflammation or suppressing inflammatory cytokine production. Provided is a device in which a weak pulse current is passed through a living body or living tissue to suppress inflammation in the living body or the living tissue. This device is provided with a power supply means, and a current control means for receiving a supply of power to intermittently apply a direct current at prescribed intervals, and is configured such that the current control means includes a pulse width modulation control means, and the pulse width modulation control
(Continued)

means generates a pulse wave that is a rectangular wave, and in which the time indicating a peak value for rising in one cycle of the pulse wave ("pulse duration") is at least 0.1 millisecond, the peak value is 1.0-20 V, inclusive, and the duty ratio of the pulse wave is at least 5.5%.

24 Claims, 9 Drawing Sheets

(51) Int. Cl.
    *A61N 1/04*     (2006.01)
    *A61N 1/08*     (2006.01)
    *A61N 2/00*     (2006.01)

(52) U.S. Cl.
    CPC ......... *A61N 1/36175* (2013.01); *A61N 2/004* (2013.01)

(56) References Cited

U.S. PATENT DOCUMENTS

| | | | |
|---|---|---|---|
| 2005/0075702 A1 | 4/2005 | Shafer | |
| 2006/0178703 A1 | 8/2006 | Huston et al. | |
| 2006/0190053 A1* | 8/2006 | Dobak | A61N 1/36167 607/44 |
| 2011/0152967 A1* | 6/2011 | Simon | A61N 2/006 607/45 |
| 2014/0028227 A1* | 1/2014 | Yasuda | H02P 27/06 318/400.17 |
| 2014/0046407 A1 | 2/2014 | Ben-Ezra et al. | |
| 2019/0224481 A1* | 7/2019 | Wingeier | A61N 1/36025 |

FOREIGN PATENT DOCUMENTS

| | | |
|---|---|---|
| JP | 2009125549 A | 6/2009 |
| WO | 2003080179 A1 | 10/2003 |
| WO | 2006073484 A2 | 7/2006 |
| WO | 2014083203 A1 | 6/2014 |

OTHER PUBLICATIONS

Morino, Saori et al., "Mild Eletrical Stimulation Increases Ubiquitinated Proteins and Hsp72 in A549 Cells via Attenuation of Proteasomal Degradation" J Pharmacol Scit, vol. 108, pp. 222-226, 2008.

Morino-Koga, Saori et al., "Insulin Receptor Activation Through its Accumulation in Lipid Rafts by Mild Electrical Stress" Journal of Cellular Physiology, vol. 228, pp. 439-446, 2008.

Fukuda, Ryosuke et al., "Mild Electrical Stimulation at 0.1-ms Pulse Width Induces p53 Protein Phosphorylation and G2 Arrest in Human Epithelial Cells" J Bid Chem, vol. 288, pp. 16117-16226, 2013.

Morino, Saori et al., "Mild Electrical Stimulation with Heat Shock Ameliorates Insulin Resistance via Enhanced Insulin Signaling" PLos One, e4068, vol. 3, Issue No. 12, pp. 1-11, Dec. 2008.

Kondo, Tatsuya et al., "Hypertermia with Mild Electrical Stimulation Protects Pancreatic . . . " Diabetes, vol. 61, pp. 838-847, Apr. 2012.

Oba, Mariko et al., "Modified Mild Heat Shock Modality Attenuates Heptic Ischemia/Reperfusion Injury" Journal of Surgical Research, vol. 162, pp. 213-220, 2010.

Koga, Tomoaki et al., "Mild Electrical Stimulation and Heat Shock Ameliorates Progressive Proteinuria and Renal Inflammation in Mouse Model of Alport Syndrome" PLos One, e43852, pp. 1-11, vol. 7, Issue No. 8, Aug. 2012.

Kondo, Tatsuya et al., "Mild Electrical Stimulation with Heat Shock Reduces Visceral Adiposity and Improves metabolic abnormalities in subjects with Metabolic Syndrome of type 2 diabetes: Randomized Crossover trials" EBioMedicine, vol. 1, pp. 80-89, 2014.

International Search Report dated Jan. 10, 2017 for International Application No. PCT/JP2016/080443.

International Preliminary Report of Patentability dated Jun. 9, 2017 for International Application No. PCT/JP2016/080443.

Fukuda, Ryosuke et al., "Mild Electrical Stimulation at 0.1-ms Pulse width induces 53 Protein Phosphorylation and G2 arrest in human Epithelial Cells" J of Biological Chemistry, vol. 288, No. 22, pp. 16117-16126, May 31, 2013.

* cited by examiner

***$P < 0.001$ vs. PMA/Io treat

*P < 0.05 vs. PMA/Io treat

DEVICE FOR SUPPRESSING INFLAMMATION AND HYPERIMMUNITY, AND METHOD FOR SUPPRESSING INFLAMMATION AND HYPERIMMUNITY

CROSS REFERENCE TO RELATED APPLICATION(S)

This application relates to, and claims the benefit and priority from International Patent Application No. PCT/JP2016/080443 filed on Oct. 13, 2017 that published as International Patent Publication No. WO 2017/065239 on Apr. 20, 2017, which claims the benefit and priority from Japanese Patent Application No. 2015-203033 filed on Oct. 14, 2016, the entire disclosures of which are incorporated herein by reference in their entireties.

FIELD OF THE DISCLOSURE

The present disclosure relates to apparatus and method for suppressing inflammation occurred in the living body, particularly, inflammation occurred by an autoimmune effect. Further, the present disclosure relates to the apparatus and method for suppressing hyperimmunization occurred in the living body.

BACKGROUND INFORMATION

All living matters existing on the earth have survived and evolved to the present age by accepting and adapting severe global environments including baking heat and extreme cold while being exposed to harsh global environmental changes from baking heat to extreme cold. Also humans are not excluded, and sense various stimuli exposed and acquire a system that can adapt to every environment in the process of evolution. It can also be said that one of the wisdom crystals of mankind making full use of this system is a medicine. However, even in modern times, there are stimuli whose acceptance mechanism has not been clarified. A representative example thereof is a weak current at a level that does not cause depolarization. Up to now, the following three matters on the action of an electric current on the living body have been clarified: (1) As an active electrical characteristic, a phenomenon accompanied by action potential generation; (2) As passive electrical characteristics, heat generation, deformation and destruction of tissue due to resistance loss; and (3) As a long-term action of an extremely weak current, supplementary effects on the original physiological functions such as actions of promoting bone development and damage healing, and the like. Of them, the mechanism of acceptance and action of the living body for the matter (3) has been completely unknown in spite of its long history and empirical knowledge of its clinical usefulness.

In recent years, however, attention has been focused on the mechanism of acceptance and action of a weak current in a living body. For example, the following reports have been made by the present inventors. It has been reported that an acceptor mechanism to recognize a weak current stimulation with a specific pulse width exists, and the weak current exerts an enhancement reaction of AKT activation under insulin stimulation (see, e.g., Non-Patent Documents 1-2) and an activating effect of p53 which is attracting attention because of a relation to chronic inflammation pathology (see, e.g., Non-Patent Document 3). It has been reported that although this optimized physical therapy does not have effects on normal animals at all, it is effective in a diabetes model (see, e.g., Non-Patent Documents 4-5, etc.), an ischemic reperfusion injury model (see, e.g., Non-Patent Document 6) and a chronic kidney disease model (see Non-Patent Document 7). Furthermore, very good results have been reported in crossover clinical trials in metabolic syndrome subjects and obese type 2 diabetes patients (see, e.g., Non-Patent Document 8).

In addition, the present inventors have proposed a living tissue normalizing apparatus that activates a normalizing function in a living body or living tissue through a heat shock protein or a ubiquitinated protein by combining a weak current and heat (38° C. to 45° C.) (see, e.g., Patent Document 1: Japanese Patent No. 5148254). Thus, there is used a pulse wave which is a rectangular wave in which the time indicating the peak value of the rising in one cycle of the pulse wave is 0.05 ms or more and 0.1 ms or less, the peak value is 3.0 V or more and 20.0 V or less and the rise time of the pulse wave is 18 nanoseconds or more and 5000 nanoseconds or less.

For example, a lot of cytokines play an important role in immune response reactions. Among them, IL-2 produced by Th1 cells has functions of activating the whole acquired immunity such as activation of Tc cells and NK cells, further, promotion of proliferation of B cells and differentiation thereof into antibody producing cells and also proliferation and differentiation of Th cells themselves, and the like, thus, contribution of IL-2 to biological defense is considered to be great. Usually, IL-2, an inflammatory cytokine that activates immunity in this way, maintains immunity homeostasis with anti-inflammatory cytokines such as IL-10 and the like. On the other hand, if the homeostasis of this immunity fails and IL-2 is produced in excess, an inflammatory response is induced, and it can be a factor promoting the onset of inflammation-related diseases. That is, to suppress and appropriately control the production of IL-2 is considered to be effective for the treatment of inflammation-related diseases (intractable autoimmune diseases, ulcerative colitis and the like).

Three transcription factors, NF-κB, AP-1 and NFAT, are coordinated for the regulation of IL-2 gene expression. When TCR on the T cell surface is stimulated, signaling downstream begins from a TCR/CD3 complex and associating tyrosine kinases and adapter molecules. PLC-γ activated by these generates DAG and IP3 by hydrolyzing PIP2, and DAG induces activation of PKC and MAPK and IP3 induces intracellular influx of calcium. Activation of PKC is induced also downstream of the co-stimulatory receptor, CD28. PKC induces intranuclear transfer of NF-κB by dissociating IκB and NF-κB (PKC/NF-κB pathway), and activation of MAPK induces the following AP-1 activation (MAPK/AP-1 pathway). On the other hand, an increase in the intracellular calcium concentration by IP3 activates calcineurin which is one of calcium/calmodulin-dependent protein kinases. Furthermore, calcineurin induces intranuclear transfer of NFAT by activating NFAT by dephosphorylation (calcium influx/NFAT pathway). Transcription factors activated downstream of these signals promote transcription of IL-2.

Recently, immunosuppressive drugs such as cyclosporin A (CsA) and tacrolimus (FK 506) are used for the treatment of autoimmune diseases and for suppression of rejection reactions at the clinical site. It is known that these drugs intend to suppress expression of IL-2 by inhibiting activation of NFAT by acting on calcineurin, and show a remarkable effect. However, since the effective therapeutic dose range is narrow and side effects such as renal toxicity and easy infectiveness become problems, monitoring of the blood drug concentration is indispensable. Moreover, since cyclosporin A and tacrolimus are metabolized by the CYP3A subfamily which is a drug metabolizing enzyme, when used in combination with drugs and foods exerting an influence on the activity of this enzyme, there is a possibility of occurrence of an increase and a decrease in the blood drug concentration, and actually, interactions with various drugs have been reported so far and combined use with a live vaccine or bosentan, a pulmonary hypertension treatment drug, is contraindicated. As described above, immunosuppressive drugs have disadvantages unique to drugs, hence, development of a more safe IL-2 production suppressing method is required.

SUMMARY OF EXEMPLARY EMBODIMENTS

Existing immunosuppressive drugs act on the normal immune system and cause side effects such as kidney damage and the like, thus, have a problem for safely controlling the hyperimmune condition. Accordingly, exemplary embodiments of the present disclosure can provide exemplary apparatus and method for suppressing the production of an inflammatory cytokine and/or exemplary apparatus and method for suppressing inflammation.

Exemplary Solution to Problem(S)

According to an exemplary embodiment of the present disclosure, it became understood that a weak pulse direct current (0.1 ms, 55 pps (pulse per second)) exerts an effect of activation of p53. It has been confirmed, according to an exemplary embodiment of the present disclosure, that the pulse direct current had no effect on the apparatus and method for suppressing IL-2 production, that is, the inflammation caused by the immune action.

Then, exemplary conditions for a weak pulse direct current have been determined, according to exemplary embodiments of the present disclosure, which can include the exemplary apparatus and method for suppressing the production of an inflammatory cytokine (e.g., IL-2) or suppressing inflammation.

In one exemplary embodiment of the present disclosure, an apparatus can be provided for passing a weak pulse direct current (pulse wave) having a specific Duty ratio through a living body or living tissue to suppress the production of an inflammatory cytokine (e.g., IL-2) or suppress inflammation in the living body or living tissue. The exemplary apparatus can be provided for passing a weak pulse current (e.g., generated by applying a direct current intermittently at a prescribed interval) through a living body or living tissue to suppress inflammation in the living body or living tissue. The exemplary apparatus can comprise a power supply device, and a current control device configured to intermittently apply a direct current at a prescribed interval in response to supply of electric power. The current control can include a pulse width modulation control device. The pulse width modulation control device can be configured as to generate a pulse wave (pulse current) which is a rectangular wave in which the time indicating the peak value of the rising in one cycle of the pulse wave (hereinafter, referred to as "pulse duration") is 0.1 ms or more, the peak value is 1.0 V or more and 20 V or less (e.g., preferably 2.0 V or more and 18 V or less, more preferably 3.0 V or more and 15 V or less) and the Duty ratio of the pulse wave is 5.5% or more.

For example, the inflammation can be an inflammation generated by the production of an inflammatory cytokine, and the above-described inflammation suppression can be based on suppression of the production of the inflammatory cytokine. Alternatively or in addition, the inflammation can be an inflammation generated by the production of any one of inflammatory cytokines IL-2, IL-6, TNF-α or INF-γ and the above-described inflammation suppression is based on suppression of the production of the inflammatory cytokine. The inflammatory cytokine can be IL-2. The intermittent interval of the direct current can be greater than 55 pps and the pulse duration can be greater than 1 ms. The pulse duration can be 10 ms or more.

In another exemplary embodiment of the present disclosure, the intermittent interval of the direct current can be greater than 550 pps, and the pulse duration can be greater than 0.1 ms. The intermittent interval of the direct current can even be 5500 pps or more. The exemplary apparatus (and the exemplary variations thereof) can be a treatment apparatus.

The apparatus according further exemplary embodiments of the present disclosure can further comprise a pair (or a plurality) of conductive pads attached to the surfaces of different sites of the living body or living tissue. For example, the current control can be further configured to generate a weak direct current intermittently between the pair (or plurality) of pads. Further, the inflammation can be based on a disease selected from the group consisting of systemic autoimmune diseases (rheumatoid arthritis, etc.) and organ-specific autoimmune diseases (psoriasis, hair loss, etc.). The exemplary apparatus can be used for the treatment of inflammation based on a disease selected from the group consisting of systemic autoimmune diseases (rheumatoid arthritis, etc.) and organ-specific autoimmune diseases (psoriasis, hair loss, etc.), and/or used in a patient receiving an immunosuppressive drug.

In another exemplary embodiment of the present disclosure, a method can be provided for passing a weak pulse direct current (pulse wave) having a specific Duty ratio through a living body or living tissue to suppress the production of an inflammatory cytokine (e.g., IL-2) or suppress inflammation in the living body or living tissue. The exemplary method can be provided for suppressing inflammation in the living body or living tissue by passing a weak pulse current (generated by applying a direct current intermittently at a prescribed interval) through a living body or living tissue. In this exemplary manner, it is possible to the shape of the pulse wave of input power to be applied is rectangle. The time indicating the peak value of the rising in one cycle of the pulse wave (hereinafter, referred to as "pulse duration") can be 0.1 ms or more, the peak value can be 1.0 V or more and 20 V or less (preferably 2.0 V or more and 18 V or less, more preferably 3.0 V or more and 15 V or less) and the Duty ratio of the pulse wave (pulse current) can be 5.5% or more.

For example, the above-described inflammation can be an inflammation generated by the production of an inflammatory cytokine and the above-described inflammation suppression is based on suppression of the production of the inflammatory cytokine. Alternatively, the inflammation can be an inflammation generated by the production of any one of inflammatory cytokines IL-2, IL-6, TNF-α or INF-γ and the above-described inflammation suppression is based on suppression of the production of the inflammatory cytokine. The inflammatory cytokine can be IL-2. The intermittent interval of the direct current can be greater than 55 pps, and the pulse duration can be greater than 1 ms. The pulse duration can be 10 ms or more. The intermittent interval of the direct current can be greater than 550 pps, and the pulse duration can be greater than 0.1 ms. Alternatively, the intermittent interval of the direct current can be 5500 pps or more. The inflammation can be based on a disease selected from the group consisting of systemic autoimmune diseases (rheumatoid arthritis, etc.) and organ-specific autoimmune diseases (psoriasis, hair loss, etc.). The exemplary method can be for the treatment of inflammation based on a disease selected from the group consisting of systemic autoimmune diseases (rheumatoid arthritis, etc.) and organ-specific autoimmune diseases (psoriasis, hair loss, etc.). Alternatively, the exemplary method can be for the treatment of inflammation in a patient receiving an immunosuppressive drug.

In another embodiment of the present disclosure, e.g., a weak pulse direct current can have a specific Duty ratio used to suppress the production of an inflammatory cytokine (e.g., IL-2) or suppress inflammation in the living body or living tissue, or use thereof. According to the exemplary embodiment of the present disclosure, the weak pulse direct current can be adapted or imparted or applied to a living body or living tissue, to suppress the production of an inflammatory cytokine (e.g., IL-2) or suppress inflammation in the living body or living tissue.

For example, a weak pulse current can be generated by applying a direct current intermittently at a prescribed interval, which can be adapted (or imparted or applied) to a living body or living tissue intermittently at a prescribed interval to suppress inflammation in the living body or living tissue. The current to be applied can have a rectangular pulse wave shape, the time indicating the peak value of the rising in one cycle of the pulse wave (hereinafter, referred to as "pulse duration") is 0.1 ms or more, the peak value can be 1.0 V or more and 20 V or less (preferably 2.0 V or more and 18 V or less, more preferably 3.0 V or more and 15 V or less) and the Duty ratio of the pulse wave (pulse current) can be 5.5% or more. The Duty ratio can be 50% or more.

The aspects described above and further aspects, features and advantages of the present disclosure may also be found in the exemplary embodiments which are described in the following with reference to the appended drawings and claims.

Exemplary Effects of Exemplary Embodiments

According to the exemplary embodiments of the present disclosure, apparatus and method for suppression of IL-2 production can be provided which is safe for living bodes is provided. The exemplary embodiments of the present disclosure also provides a way of suppressing inflammation (for example, based on immunological effect).

The exemplary embodiments of the present disclosure can further be used in combination with immunosuppressive drugs, and can reduce the amount of the immunosuppressive drug used and suppress occurrence of side effects.

BRIEF DESCRIPTION OF DRAWINGS

Further exemplary embodiments of the present disclosure are detailed in the description of the Figures, where this description shall not limit the scope of the present disclosure. The Figures show.

Figure 1:
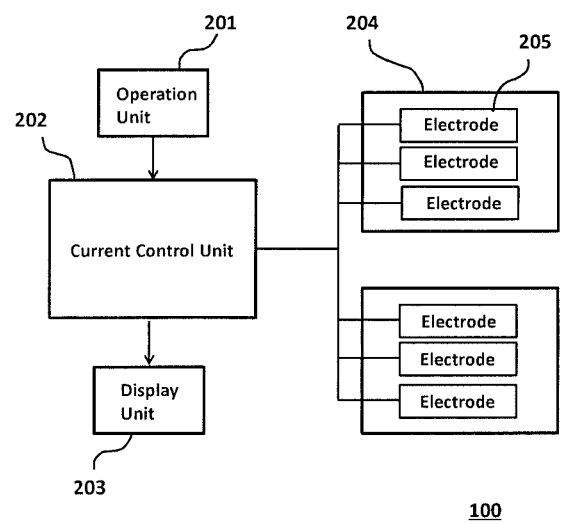
FIG. 1 is an overall schematic configuration diagram of a treatment apparatus according to an exemplary embodiment of the apparatus of the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described embodiments without departing from the true scope and spirit of the subject disclosure as defined by the appended claims.

DETAILED DESCRIPTION OF EXEMPLARY EMBODIMENTS

Hereinafter, exemplary embodiments of the present disclosure will be illustrated and described in detail with reference to the exemplary embodiments, along with the preferred methods and materials which can be used in practice of the present disclosure. Unless otherwise specified in the sentences, any technical terms and scientific terms used in the present specification, have the same meaning as those generally understood by those of ordinary skill in the art to which the present disclosure belongs. Further any materials and methods equivalent or similar to those described in the present specification can be used for practicing the present disclosure. Furthermore, all publications and patents cited herein in connection with the present disclosure described herein are incorporated herein by reference, for example, as indicating methodology, materials, etc. that can be used in the exemplary embodiments of the present disclosure.

According to exemplary embodiments of the present disclosure, a weak pulse current generated by intermittently applying a direct current at a prescribed interval can have a Duty ratio of 5.5% or more, preferably 10% or more, more preferably 20% or more, further preferably 30% or more, particularly preferably 50% or more. The upper limit of the Duty ratio of the pulse current is not particularly limited as far as suppression of inflammation is exhibited, but it is preferably 90% or less, more preferably 80% or less, from the performance of the control apparatus and other factors.

The pulse wave of the input current applied is a rectangular wave, and the time indicating the peak value of the rising in one cycle of the pulse wave ("pulse duration") is 0.1 ms or more, preferably greater than 0.1 ms, more preferably 0.2 ms or more, further preferably 1 ms or more, particularly preferably 10 ms or more.

The voltage of the peak value is preferably 1.0 V or more and 20.0 V or less, the lower limit is more preferably 2.0 V or more, further preferably 3.0 V or more, particularly preferably 6.0 V or more, and the upper limit is more preferably 18 V or less, further preferably 15 V or less. A function generator may be used for input of voltage. By this, it is possible to apply the input voltage accurately and it is possible to simplify the circuit.

In the apparatus according to the present disclosure, the pad 204 on which the electrode 205 for passing specific weak pulse direct current through a living body or living tissue of is disposed is applied (for example, pasted) to peripheral parts of the target inflammatory site including, for example, but not limited to, target areas chosen from head, face, neck, shoulder, body trunk, chest, abdomen, arm, wrist, hand, waist, knee, lower leg, ankle and foot of a patient.

Inflammation can be suppressed by passing a prescribed specific weak pulse direct current for an arbitrary time using the apparatus of the present disclosure.

The apparatus according to the present disclosure can further comprise a heat generating layer in the pad 204, and exert a hyperthermic effect on the target tissue. In this case, the hyperthermic effect can be attained if, for example, a pair of electrodes are each formed into a strip shape and a resistance between the electrodes is formed of a carbon fiber having an orientation in a direction parallel to the strip-shaped electrodes in the heat generating layer.

Since a pair of electrodes are each formed into a strip shape and a resistance between the electrodes is formed of a carbon fiber having an orientation in a direction parallel to the strip-shaped electrodes in the heat generating layer of the pad as described above, heat generation can be attained by appropriate resistance value between carbon fibers which are mutually parallel without occurring short circuit between the electrodes by the carbon fiber, thus, the hyperthermic effect can be obtained in addition to the effect of the present disclosure.

The apparatus according to exemplary embodiments of the present disclosure can comprise a current control unit 202 for intermittently supplying a direct current to the electrodes 205 in the pad at an arbitrary cycle and an operation unit 201 for operating the current control unit 202, and further can comprise a display unit 203 for monitoring the supplied current. Power is supplied from a power supply means (not shown in the drawing) to the current control unit 202 to generate a current. The current control unit 202 is provided with a current control device. The current control device intermittently controls the supply of the direct current supplied to the electrode 205 at a cycle capable of providing the prescribed Duty ratio. The current control means further includes a pulse width modulation control means, thereby generating a pulse wave having an arbitrary height (amplitude). The pulse width modulation control device generates an intermittent pulse wave (pulse current) at an arbitrary cycle, for example, but not limited to 55 pps or more, 550 pps or more or 5500 pps or more for an arbitrary pulse duration, for example, but not limited to 0.1 ms, 1 ms or 10 ms. The Duty ratio is, for example, 5.5% if the pulse duration is 0.1 ms and the cycle is 550 pps. The pulse duration and the cycle are selected so that the Duty ratio is 5.5% or more, preferably 10% or more, more preferably 20% or more, further preferably 30% or more, particularly preferably 50% or more. More specifically, if the pulse duration is 0.1 ms, the cycle is 550 pps or more, preferably 5500 pps or more, and when the pulse duration is 1.0 ms, the cycle is 55 pps or more, preferably 550 pps or more, and when the pulse duration is 10 ms, a preferable result can be obtained even at 55 pps.

In the case where heat is used simultaneously in the treatment apparatus according to the present disclosure, it is desirable that each heat generating layer in the pair of pads is heated to 38° C. or higher and 45° C. or lower. When the heating temperature is 38° C. or higher and 45° C. or lower, thermal stimulation can be moderately given to a living body or living tissue, and the treatment can be performed effectively.

In the apparatus of the present disclosure, the above-described pad is not particularly limited as long as a pulse direct current with a prescribed Duty ratio can be applied to a living body or tissue in a living body, but it is preferable that the pad is made of a substance having low irritation to the living body. Further, electromagnetic wave shielding rubber that generates far infrared ray may be used, and in this case, thermal stimulation can also be achieved easily.

The apparatus according to the present disclosure is characterized by applying and passing a weak pulse direct current with a Duty ratio of 5.5% or more through the target living body or living tissue, thereby suppressing inflammation caused by the production of an inflammatory cytokine. The type and conditions of the weak pulse direct current are as described above already.

The inflammatory cytokine includes, but not limited to, for example, IL-2, IL-4, IL-6, IL-13, IFN-$\gamma$ and TNF-$\alpha$, and the apparatus according to the present disclosure is characterized by suppressing the production of at least one of these inflammatory cytokines, and particularly, can effectively suppress production of IL-2.

These cytokines are responsible for autoimmune diseases, and the apparatus according to the present disclosure is suitable for the treatment of autoimmune diseases.

In addition, the apparatus according to the present disclosure can suppress inflammation in the treatment of diseases including, but not limited to, for example, systemic autoimmune diseases (rheumatoid arthritis, etc.), organ-specific autoimmune diseases (psoriasis, hair loss, etc.) and the like, and is suitable for the treatment or prevention of these diseases.

In use of the apparatus according to an exemplary embodiment of the present disclosure, a pad for passing a prescribed weak pulse direct current can be pasted to a part of a living body where inflammation is caused (including, but not limited to, for example, knee, leg, arm, and other parts). The apparatus of the present disclosure can also be used in a living body site where inflammation is expected to be caused so as to prevent or reduce inflammation. Further, by using a biocompatible pad material as a material, it is also possible to apply the pad portion of the apparatus of the present disclosure in a living body.

When describing, for example, rheumatoid arthritis, a pad of the apparatus of the present disclosure can be pasted to the joint portion where rheumatoid arthritis is caused, for example, to the left and right sides of knee, to pass a prescribed weak pulse direct current through the portion, although the operation is not limited to this.

In the case of diseases caused by inflammation caused by inflammatory cytokines in a living body, the treatment and prevention of the diseases can be performed by suppressing inflammation in a living body using the apparatus according to an exemplary embodiment of the present disclosure. For example, by applying the apparatus according to an exemplary embodiment of the present disclosure to the head, also diseases caused by inflammation due to inflammatory cytokines in the brain, for example, Alzheimer disease, can be treated or prevented.

The method according to an exemplary embodiment of the present disclosure can be characterized by applying and passing a weak pulse direct current with a Duty ratio of 5.5% or more through the target living body or living tissue, thereby suppressing inflammation caused by the production of an inflammatory cytokine. The type and conditions of the weak pulse direct current are as described above already. In addition, inflammatory cytokines that can be suppressed and applicable diseases are also as described herein.

In order to pass the weak pulse direct current with the above-described Duty ratio through an living body based on the method according to an exemplary embodiment of the present disclosure, a commercially available apparatus capable of passing an electric current through an living body can be improved and a weak pulse direct current having the target Duty ratio can be applied.

Further, an exemplary embodiment of the present disclosure relates to a weak pulse direct current having a Duty ratio of 5.5% or more used for suppressing inflammation caused by the production of an inflammatory cytokine occurred in a living body or living tissue, by adapting or imparting or applying to the target living body or living tissue transdermally, or the use of the weak pulse direct current. The type and conditions of the weak pulse direct current are as described above already. In addition, inflammatory cytokines that can be suppressed and applicable diseases are also as described herein.

The weak pulse direct current having a Duty ratio of 5.5% or more used in the present disclosure does not apply load on a person receiving electricity, since this current is safe for a living body and gives a sensation of from comfort to no stimulation when applied to a living body.

The apparatus and method according to exemplary embodiments of the present disclosure can also be used in combination with an immunosuppressive drug. By using them in combination, it is possible to reduce the amount of immunosuppressive drugs used and to suppress the occurrence of side effects. The immunosuppressive drug includes, but not limited to, cyclosporin A (CsA), tacrolimus (FK 506) and the like.

EXAMPLES

Hereinafter, exemplary embodiments of the present disclosure will be specifically described with reference to examples, but the present disclosure is certainly not limited to the following examples or exemplary embodiments.

Materials and Experimental Methods

1. Experimental Apparatus Model

Figure 2:
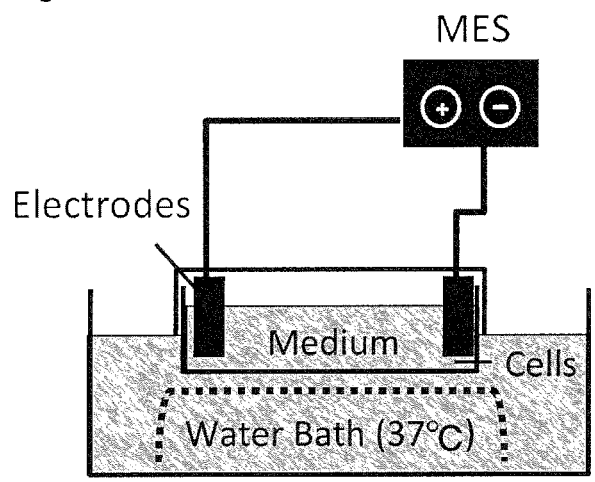
FIG. 2 is a model diagram of a weak current (MES) generator used in an in vitro experiment of the exemplary embodiment.

A model diagram of an apparatus used in in vitro experiments using cultured cells is shown in FIG. 2. MES in the figure shows a low voltage pulse current (MES) generator. A hole for electrodes was drilled in the lid of the plastic culture dish, the electrode was passed through the hole and the electrode was immersed in the culture solution. For the electrode, electromagnetic wave shielding rubber that generates infrared ray manufactured by Tsuchiya Rubber Co., Ltd. was used. The side face of the dish was covered with a tape and the dish was immersed in a thermostat bath of 37° C. and the temperature of the culture solution was kept constant. The treatment time was usually 10 minutes.

2. Cells and Culture Conditions

Jurkat cells, a human acute T cell leukemia cell line obtained from ATCC and BV2 cells, a mouse microglial cell line obtained from ATCC were used and cultured using RPMI-1640 (Wako) as a basal culture medium. The cells were statically cultured at a cell number not exceeding 3×10$^6$ cells/mL. In the experiment, a serum-free culture medium was used, and cell death was confirmed by Trypan blue staining.

3. Total RNA extraction from cultured cells

Jurkat cells (or BV2 cells) were seeded at a rate of 3 to 5×10$^6$ cells/dish in a 35 mm plastic culture dish and an experiment was conducted. MES was applied at 37° C. for 10 minutes, and directly after, the cells were treated with a T cell activator and cultured at 37° C. for 3 hours, then, the total RNA was extracted using RNAiso plus (registered trademark) (Takara), according to the protocol of the manufacturer.

4. Quantitative RT-PCR method

RT-PCR was performed using the total RNA extracted from cultured cells. For the RT reaction, PrimeScript (registered trademark) RT reagent Kit (Perfect real time) (Takara) or PrimeScript (registered trademark) RT Master Mix (Perfect real time) (Takara) was used, and for the PCR reaction, SYBR (registered trademark) Premix EX Taq™ II (Tli RNaseH Plus) (Takara) was used. Further, in order to compare the expression level of mRNA between samples, β-actin was used as an internal control. The method was carried out according to the protocol of the manufacturer. The conditions are as follows: reverse transcription reaction (37° C. for 30 minutes, 85° C. for 10 seconds), PCR reaction (95° C. for 3 minutes, [95° C. for 10 minutes, 60° C. for 1 minute]×40 cycles/amplification reaction, 65 to 95° C. for 10 seconds/melting reaction). As the primer (sense sequence, antisense sequence), human IL-2, human INF-□, human IL-10, human CCL-3, human TRAF-1 and □-actin were used.

5. Extraction of protein from cultured cells and measurement of concentration thereof After culturing under the same conditions as in 3, proteins were collected according to a conventional method and proteins were quantified using the BCA method to make the protein amount of each sample constant.

6. Extraction of nuclear protein from cultured cells and measurement of concentration thereof After culturing under the same conditions as in 3, nuclear proteins were collected according to a conventional method and proteins were quantified using the Bradford method to make the protein amount of each sample constant.

7. Western blotting

Proteins extracted from cultured cells were used as samples, the protein amount of each sample was kept constant, and Western blotting was performed according to a conventional method. Primary antibodies and secondary antibodies used are shown below.

Primary Antibodies: Rabbit anti-phospho-IκB-α (Ser32), Rabbit anti-IκB-α, Mouse anti-NF-κB p65, Mouse anti-NF-κB p50, Rabbit anti-NFAT1, Rabbit anti-phospho-AMPK-α (Thr172), Rabbit anti-AMPK-α, Rabbit anti-phospho-JNK (Thr183/Tyr185), Rabbit anti-JNK, Rabbit anti-phospho-p38 (Thr180/Tyr182), Rabbit anti-p38, Rabbit anti-phospho-ERK1/2 (Thr202/Tyr185), and Rabbit anti-ERK1/2 (purchased from Cell Signaling Technology, Inc.), Mouse Ubiquitinated protein (purchased from BIOMOL, Inc.), Goat anti-β-actin, and Goat anti-γ-tubulin (purchased from SANTA CRUZ BIOTECHNOLOGY, Inc.)

Secondary Antibodies: Anti-rabbit IgG-HRP, Anti-mouse IgG-HRP, and Anti-goat IgG-HRP (purchased from Jackson Immuno Research LABORATORIES, Inc.)

8. ELISA Method

Jurkat cells were seeded at a ratio of 3×106 cells/dish in a 35 mm plastic culture dish and experiments were carried out. MES was applied at 37° C. for 10 minutes, and directly after, the cells were treated with a T cell activator and cultured at 37° C. for 24 hours, then, the culture solution was collected and centrifugal separation (4° C., 12,000 rpm, 10 minutes) was carried out. A 1% v/v Protease inhibitor cocktail was added to the supernatant to prepare a sample. Cytokine production was quantified using an ELISA method.

Example 1: Effect of MES on PMA/Io-Induced IL-2 Production (1) Effects of alternating current (MAES) and direct current (MDES)

A weak current (mild electrical stress: MES) was examined whether suppressing the production of inflammatory cytokines by acting directly on immune cells. We focused on IL-2 which is one of the major inflammatory cytokines produced by T cells and also is a target molecule for immunosuppressive drugs and used, as an IL-2 production inducing agent, PMA (Phorbol 12-myristate 13-acetate), an activator of PKC and Ionomycin (Io), a calcium ionophore. Currents are roughly divided into two types, an alternating current (MAES) whose magnitude and direction periodically change with time and a direct current (MDES) in which flow direction (positive or negative) does not change even if magnitude varies with time, therefore, we investigated whether differences between these current condition affect the IL-2 production suppressing effect.

Figure 3:
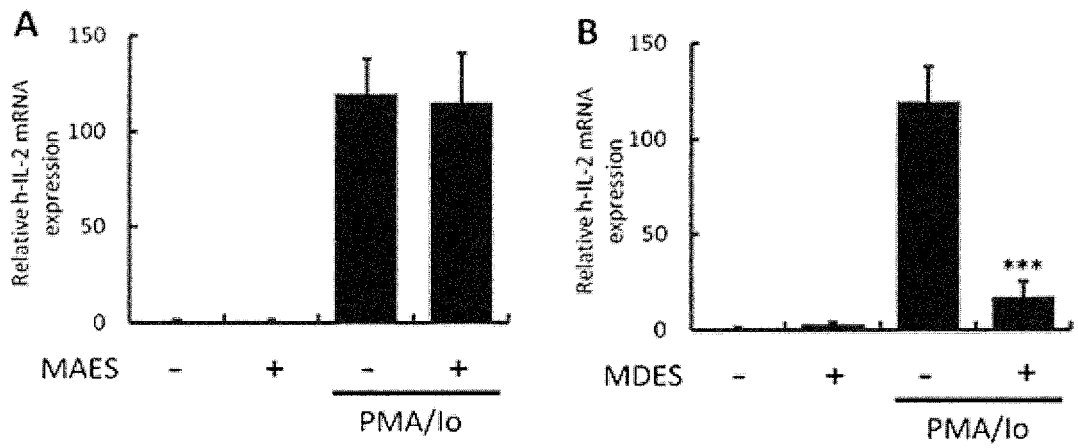
FIG. 3 is an illustration of exemplary results of confirmation of the effect of an alternating current (MAES) and a direct current (MDES) on PMA/Io-induced IL-2 production. The expression level of mRNA is standardized with β-actin mRNA. The data represent the results of 3 experiments in each group.

Jurkat cells were seeded at a rate of 5×106 cells/dish in a 35 mm dish, and MES (MAES, MDES) treatment was carried out under conditions of 6 V, 37° C. and 10 minutes. Immediately after the MES treatment, the cells were treated with PMA (10 nM) and Ionomycin (500 nM) in combination (PMA/Io), cultured at 37° C. for 3 hours, then, the total RNA was collected, and the expression levels of IL-2 mRNA were measured and compared by a quantitative RT-PCR method. The results are shown in FIG. 3. As a result, though MAES showed no suppressive effect on IL-2 production induced by PMA/Io, MDES significantly suppressed PMA/Io-induced IL-2 production while not affecting the steady-state IL-2 expression level. From these results, it became clear that MES suppresses IL-2 production by directly acting on T cells. The effect was observed only with a direct current, but not with an alternating current.

(2) Effect of MPES (55 pps)

Figure 4:
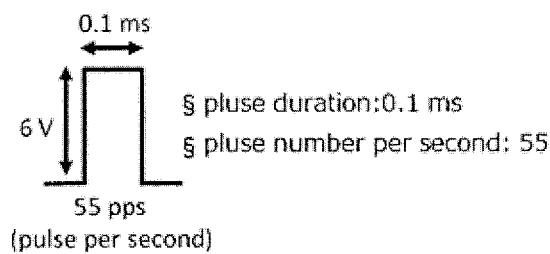
FIG. 4 is an illustration of exemplary results of the effect of a pulse direct current (MPES; 0.1 ms, 55 pps) on PMA/Io-induced IL-2 production, as the expression level of mRNA is standardized with β-actin mRNA, and the data represent the results of 3 experiments in each group.
Figure 4:
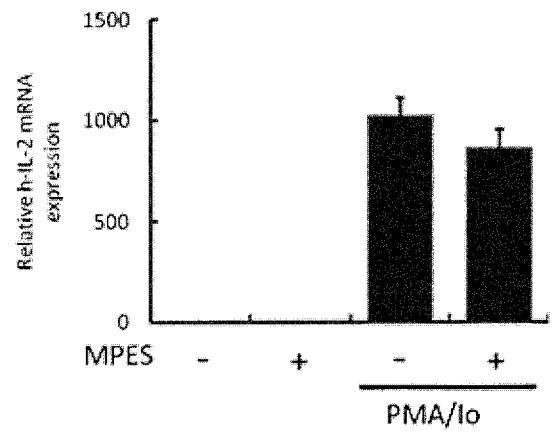

Since a pulse direct current (MPES) also exists in the waveform of a direct current, we subsequently examined whether MPES suppresses the production of inflammatory cytokines by acting directly on immune cells. For a pulse direct current, a condition which gives a rectangular wave having a pulse duration of 0.1 ms 55 times per second (55 pps) (Duty ratio=0.55%) was used. The expression levels of IL-2 mRNA were compared under the same conditions as described above excepting MES. The results are shown in FIG. 4. As a result, MPES (0.1 ms, 55 pps) showed no significant suppressive effect on IL-2 production induced by PMA/Io.

(3) Effect of MPES (Pulse Duration 1 ms, 10 ms)

Figure 5:
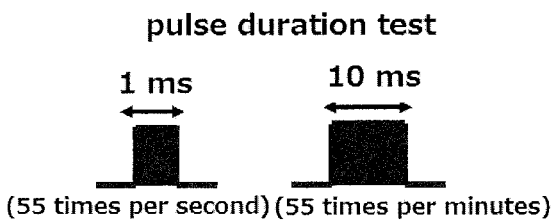
FIG. 5 is an illustration of exemplary results of the effect of a pulse direct current (MPES) on PMA/Io-induced IL-2 production with varying the pulse duration, the expression level of mRNA is standardized with β-actin mRNA, and the data represent the results of 3 experiments in each group.
Figure 5:
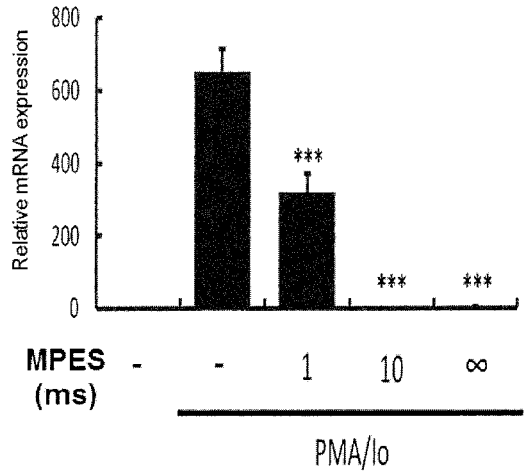

Next, the pulse duration was examined. The expression levels of IL-2 mRNA were measured and compared in the same manner as described above. As MES, MPES with a pulse duration of 1 ms or 10 ms (6 Vp-p, 55 Pps) (Duty ratio=5.5%, 55%, respectively) or MDES (duration: □) (Duty ratio=100%) was used. The results are shown in FIG. 5. As a result, a more remarkable suppressive effect on IL-2 production induced by PMA/Io was observed under the condition of longer pulse duration (10 ms).

(4) Effect of MPES (Pulse Wave Number 550 Pps, 5500 Pps)

Figure 6:
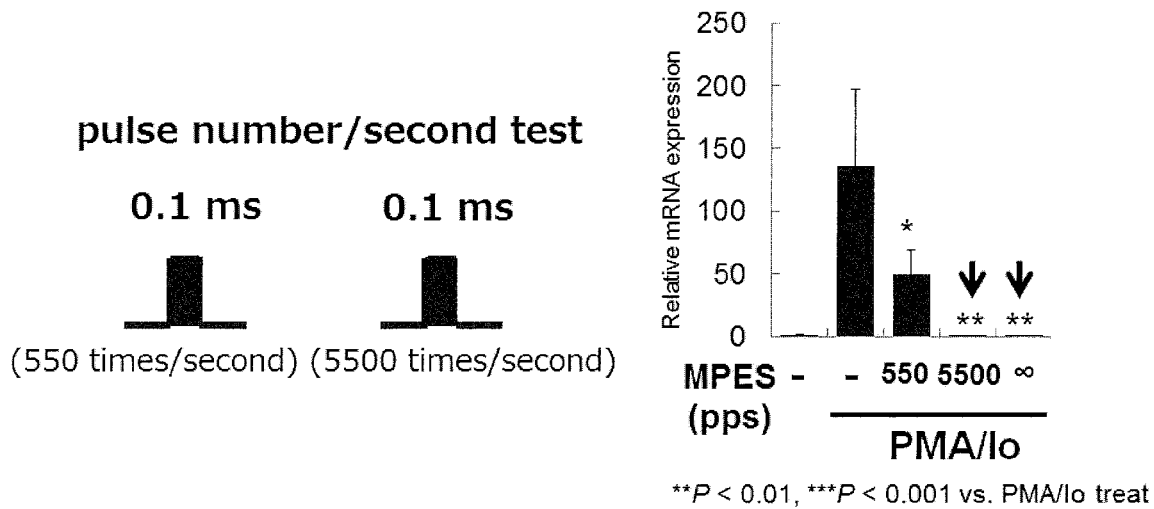
FIG. 6 is an illustration of exemplary results of the effect of a pulse direct current (MPES) on PMA/Io-induced IL-2 production with varying the pulse number, the expression level of mRNA is standardized with β-actin mRNA, and the data represent the results of 3 experiments in each group.

Next, the number of pulses per second was examined. The expression levels of IL-2 mRNA were measured and compared in the same manner as described above. As MES, MPES with a pulse wave number of 550 pps or 5500 pps (6 Vp-p, 0.1 ms) (Duty ratio=5.5%, 55% respectively) or MDES (pulse rate: □) (Duty ratio=100%) was used. The results are shown in FIG. 6. As a result, a more remarkable suppressive effect on IL-2 production induced by PMA/Io was observed under the condition of larger number of pulses per second (5500 pps).

(5) Effect of MDES (voltage: 3 V, 6 V)

Figure 7:
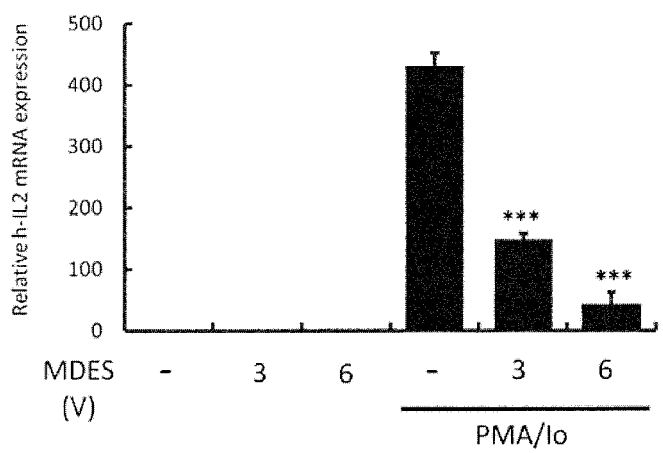
FIG. 7 is an illustration of exemplary results of the effect of a direct current (MDES) on PMA/Io-induced IL-2 production with varying the voltage, the expression level of mRNA is standardized with β-actin mRNA, and the data represent the results of 3 experiments in each group.

Furthermore, the influence of the magnitude of the voltage on the effect of suppressing IL-2 production by MDES was examined. The expression levels of IL-2 mRNA were measured and compared in the same manner as described above. The MDES treatment was performed under conditions of 3 V or 6 V, 37° C. and 10 minutes. The results are shown in FIG. 7. As a result, the effect of suppressing IL-2 production by MDES was observed in a voltage-dependent manner. Further, MDES of 9V showed about the same degree of the IL-2 production suppressing effect as that of MDES of 6 V (data not shown), though it is a preliminary investigation.

(6) Effect of Suppression of IL-2 Protein Production

Figure 8:
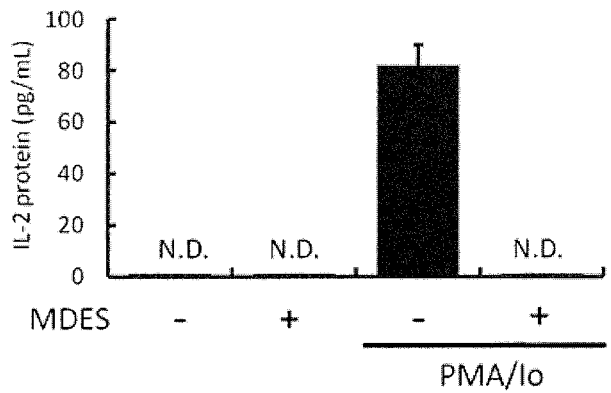
FIG. 8 is an illustration of exemplary results of the effect of a direct current (MDES) on PMA/Io-induced IL-2 protein production, the data represent the results of 3 experiments in each group, and N. D. represents a value below the detection limit.

We investigated whether the IL-2 production suppressing effect by MDES is recognized also at the protein level. Cells were cultured in the same manner as described above and the cell culture medium was collected after culturing for 24 hours and the amounts of the IL-2 protein secreted in the cell culture medium were measured and compared using an ELISA method. The results are shown in FIG. 8. As a result, MDES suppressed PMA/Io-induced IL-2 production even at the protein level.

Example 2: Effect of MES on TCR Stimulation-Induced IL-2 Production

Generally, T cells in a living body are activated by stimulation of TCR/CD3 complex and CD28 by antigen presenting cells. Then, we examined whether MDES shows the suppressive effect on also IL-2 production induced upon stimulation of TCR/CD3 complex and CD28. As the stimulation, 1 □g/ml anti-human CD3 antibody and 1 □g/ml anti-human CD28 antibody (CD3/CD28) were used.

Figure 9:
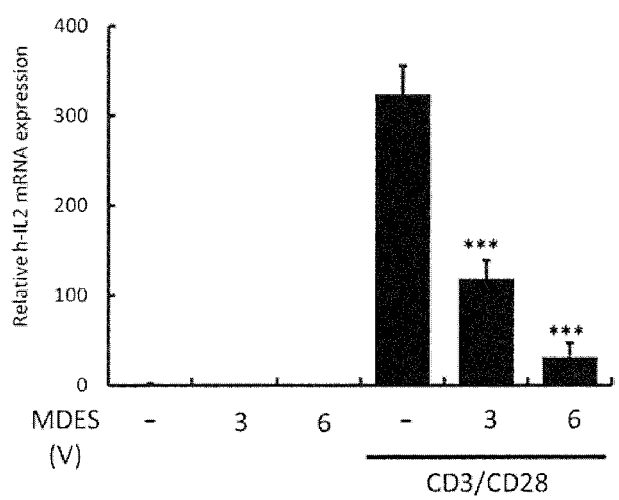
FIG. 9 is an illustration of exemplary results of the effect of a direct current (MDES) on CD3/CD28-induced IL-2 production with varying the voltage, the expression level of mRNA is standardized with β-actin mRNA, and the data represent the results of 3 experiments in each group.

Jurkat cells were seeded at a rate of 4×106 cells/dish in a 35 mm in dish and the MDES treatment was performed under conditions of 3 V or 6 V, 37° C. and 10 minutes. Immediately after the MDES treatment, the cells were treated with CD3/CD28 and cultured at 37° C. for 3 hours, then, the total RNA was collected and the expression levels of IL-2 mRNA were measured and compared by a quantitative RT-PCR method. The results are shown in FIG. 9. As a result, MDES suppressed IL-2 production in a voltage-dependent manner even under CD3/CD28 stimulation.

Example 3: Effect of MES on Inflammation Related Factor Production

Figure 10:
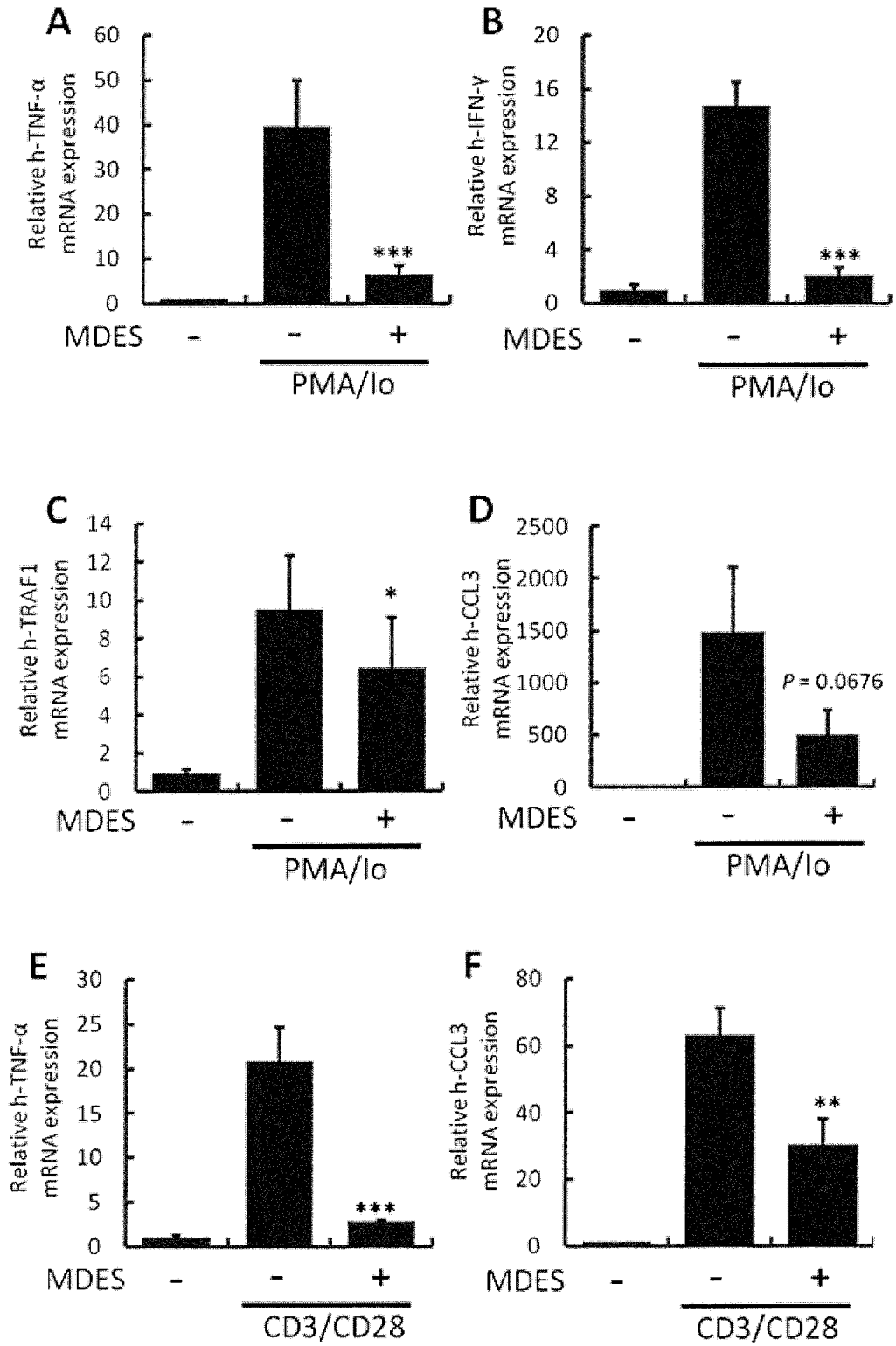
FIG. 10 is an illustration of exemplary results of the effect of a direct current (MDES) on PMA/Io or CD3/CD28-induced inflammatory cytokine (TNF-α, IFN-γ, TRAF1, CCL3) production, the expression level of mRNA is standardized with β-actin mRNA, and the data represent the results of 3 experiments in each group.

The suppressive effect of MDES on production of T cell activator-induced cytokines and chemokines other than IL-2 was examined. Jurkat cells was seeded at a rate of 4×106 cells/dish in a 35 mm dish, and the MDES treatment was performed under conditions of 6 V, 37° C. for 10 minutes. Immediately after the treatment, the cells were treated with PMA/Io or CD3/CD28 and cultured at 37° C. for 3 hours, then, the total RNA was collected and the expression levels of each mRNA were measured and compared by a quantitative RT-PCR method. The results are shown in FIG. 10. As a result, it was shown that MDES suppresses or tends to suppress the production of cytokines and chemokines other than IL-2 such as TNF-α, IFN-γ, TRAF1, CCL3 and the like. Therefore, it was suggested that MDES comprehensively suppresses inflammatory cytokine production.

Example 4: Comparison of Suppressive Effects on Inflammatory Cytokine Production Between MES and Existing Immunosuppressive Drugs Immunosuppressive drugs currently in clinical use include CsA and FK 506. These drugs suppress activation of NFAT, a transcription factor of IL-2, by strongly inhibiting calcineurin. In order to compare the usefulness of MDES and these immunosuppressive drugs, we examined the degree of IL-2 production suppressing effect as an indicator. The concentration of each immunosuppressive drug was adjusted in a range (0.1 □M to 1 □M) wherein TCR stimulation-induced IL-2 production is suppressed effectively, but cytotoxicity such as apoptosis induction against T cells in the steady state and the activated state is not observed.

Figure 11:
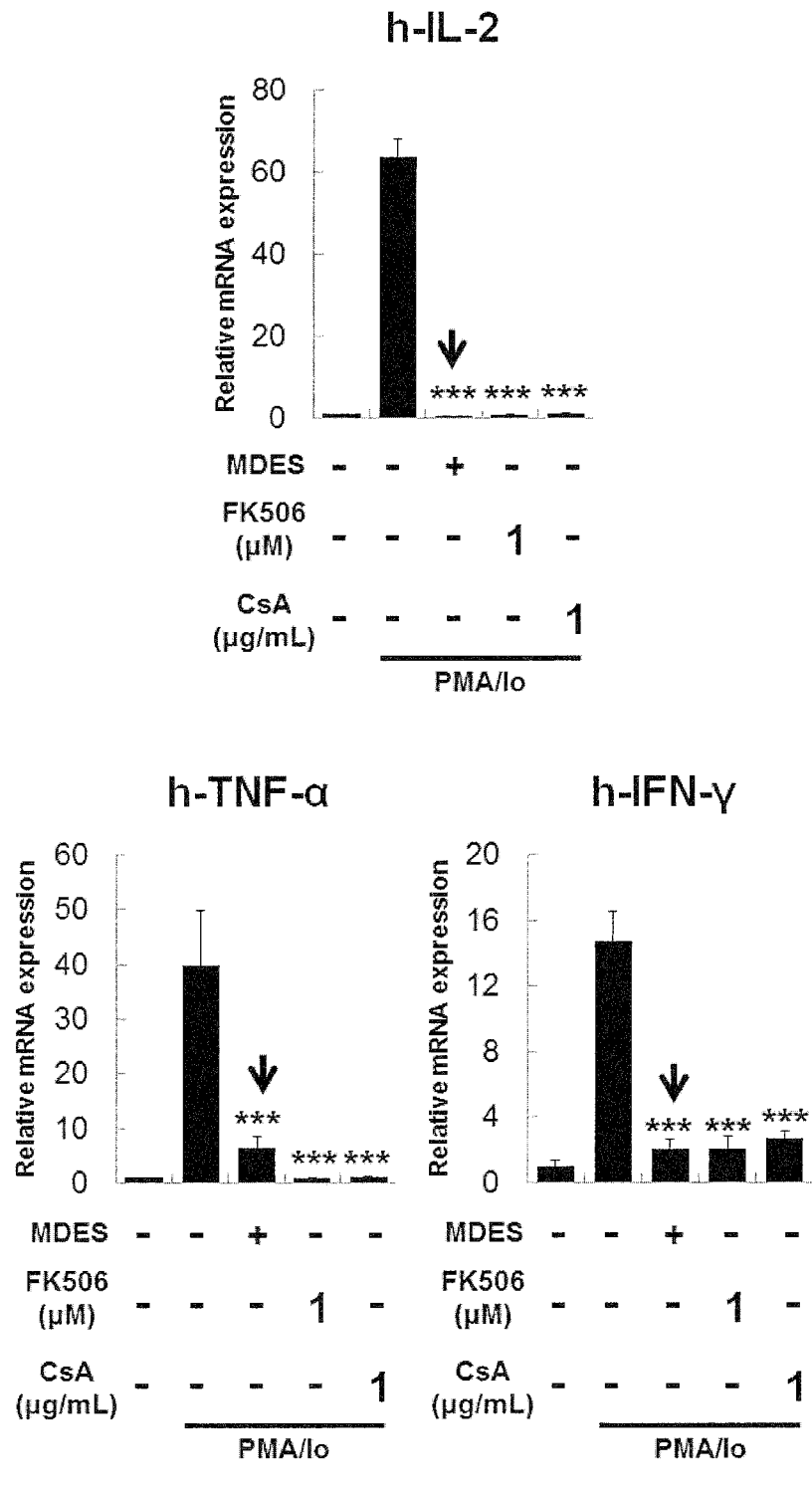
FIG. 11 is an illustration of exemplary results of comparison of the effects of suppressing the production of inflammatory cytokines between MDES and existing immunosuppressive drugs (F 506, CsA), the expression level of mRNA is standardized with β-actin mRNA, and the data represent the results of 3 experiments in each group.

Jurkat cells were seeded at a rate of 4×106 cells/dish in a 35 mm dish, and treated with 1 □M FK506 or 1 □g/mL (ca. 0.83 □M) CsA, then, cultured at 37° C. for 1 hour, or the MDES treatment was performed under conditions of 6 V, 37° C. for 10 minutes. Thereafter, the cells were treated with PMA/Io, cultured at 37° C. for 3 hours, and the total RNA was collected and the expression levels of IL-2, TNF-α and IFN-γ were measured and compared by a quantitative RT-PCR method. The results are shown in FIG. 11. As a result, MES showed the suppressive effect of IL-2, TNF-α and IFN-γ production comparable to existing immunosuppressive drugs treated for 4 hours. Therefore, it was suggested that MES has the same usefulness as existing immunosuppressive drugs.

Example 5: Effect of HS (Heat Shock) on PMA/Io-Induced IL-2 Production

Figure 12:
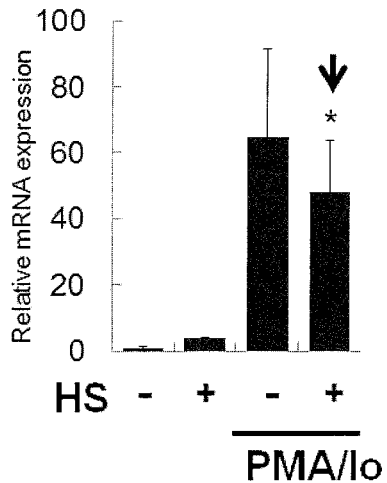
FIG. 12 is an illustration of exemplary results of the effect of heat on PMA/Io-induced IL-2 production, the expression level of mRNA is standardized with β-actin, and the data represent the results of 3 experiments in each group.

We investigated whether HS suppresses the production of inflammatory cytokines by directly acting on immune cells. Jurkat cells were seeded at a rate of 3×106 cells/dish in a 35 mm dish, and the HS treatment was performed under conditions of 42° C. for 10 minutes. Directly after the HS treatment, the cells were treated with PMA/Io, cultured at 37° C. for 3 hours, then, the total RNA was collected and the expression levels of IL-2 mRNA were measured and compared by a quantitative RT-PCR method. The results are shown in FIG. 12. As a result, HS suppressed PMA/Io-induced IL-2 production.

Comparative Example: Test Using Inflammatory Mouse Model Induced by Concanavalin a Concanavalin A activates T cells and induces the production of IL-2, INF-γ and other cytokines derived from T cells. In the concanavalin A-administered model, these cytokines accumulate in the liver and spleen, causing inflammation.

We investigated whether MES suppresses the production of inflammatory cytokines in the spleen and liver of the concanavalin A-administered mouse model. BALB/c mice were treated with MES at 2 V/cm for 10 minutes. The MES treatment was performed under the conditions of MPES (0.1 ms; 55 pps) (Duty ratio=0.55%) and MDES (duration: □) (Duty ratio=100%). Thereafter, concanavalin A (ConA) was intravenously administered in an amount of 5 mg/kg, and after 4 hours, the total RNA was extracted from mouse spleen and the expression levels of IL-2 and IFN-γ were measured and compared by a quantitative RT-PCR method.

Figure 13:
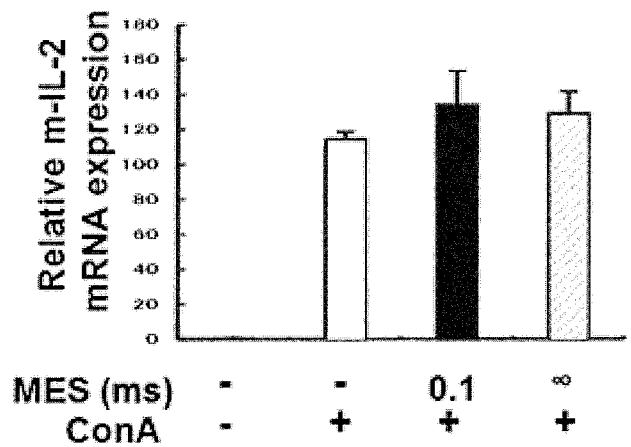
FIG. 13 is an illustration of exemplary results of the effect of direct current (MES: MDES and MPES) on inflammatory cytokine (IL-2, IFN-γ) production using an inflammatory mouse model induced by concanavalin A, the expression level of mRNA is standardized with HPRT mRNA, and the data represent the results of 6 experiments in each group.
Figure 13:
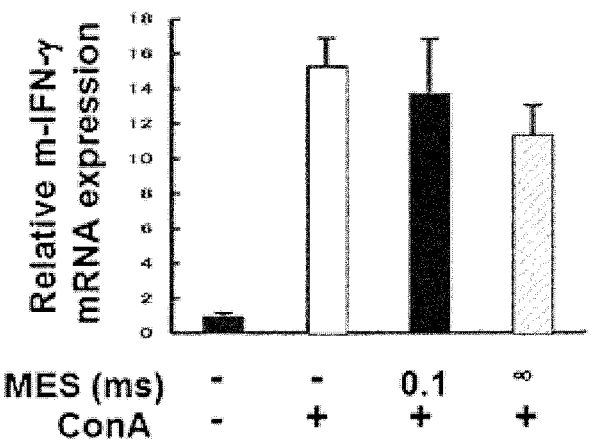
Figure 14:
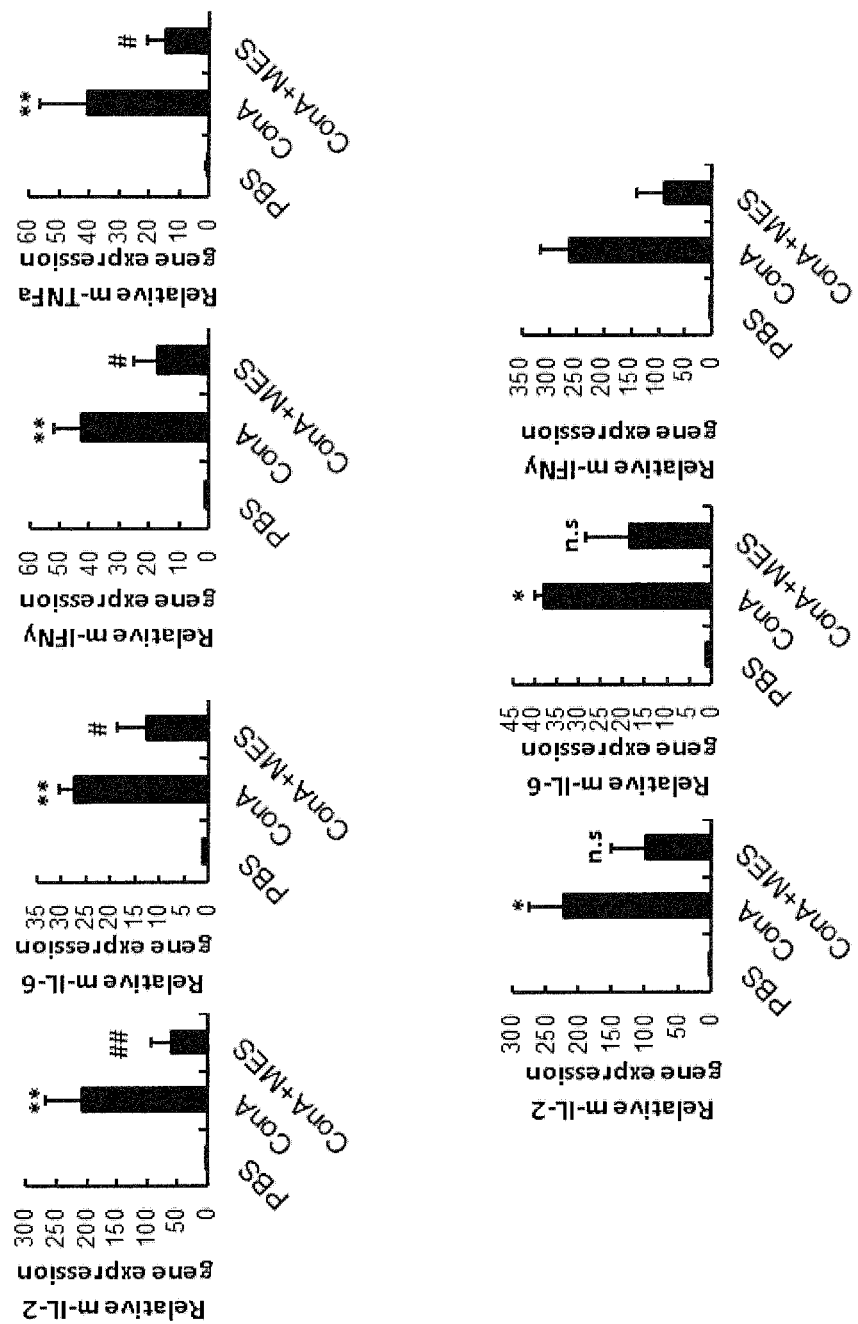
FIG. 14 is an illustration of exemplary results of the effect of a direct current (MES: MPES) on the production of various inflammatory cytokines (IL-2, IL-6, IFN-γ, TNF-α) using an inflammatory mouse model induced by concanavalin A, the expression level of mRNA is standardized with GDPDH mRNA, and the data represent the results of 8 experiments in each group for spleen and 4 experiments in each group for liver.

PBS was used as a control for ConA. The results are shown in FIG. 13. As a result, MES did not suppress cytokine production, under the above-described conditions Example 7: Test Using Inflammatory Mouse Model Induced by Concanavalin A We investigated whether MPES with a Duty ratio above a specific value suppresses the production of inflammatory cytokines in the spleen and liver of the concanavalin A-administered mouse model. BALB/c mice were treated with MPES (duration: 0.1 ms; 5500 pps) (Duty ratio=55%) at 4 V/cm for 20 minutes. Thereafter, concanavalin A (ConA) was intravenously administered in an amount of 1 mg/kg, and the mice were treated with MES again under the same conditions. Four hours after the MES treatment, the total RNA was extracted from mouse spleen and liver and the expression levels of IL-2, IL-6, IFN-γ and TNF-α were measured and compared by a quantitative RT-PCR method. PBS was used as a control for ConA. The results are shown in FIG. 14 (upper row: spleen; lower row: liver). As a result, MES suppressed cytokine production. Sections of tissue of spleen and liver 8 hours after administration of ConA were stained with H&E. MES showed an improvement of inflammation (data not shown). By this, MES improved inflammation induced by ConA.

Figure 15:
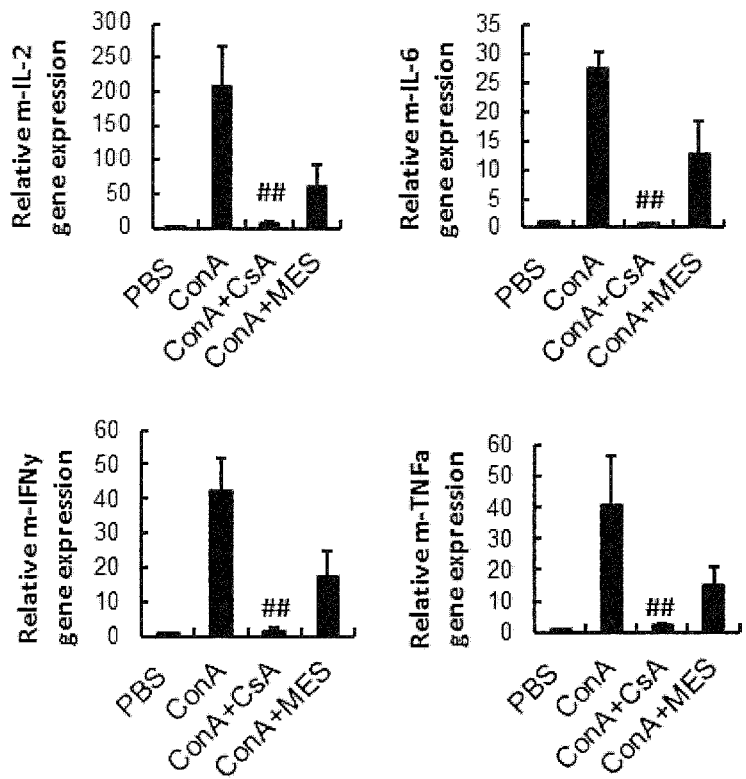
FIG. 15 is an illustration of exemplary results of comparison of the effects of suppressing the production of inflammatory cytokines between a direct current (MES: MPES) and an existing immunosuppressive drug (CsA), using an inflammatory mouse model induced by concanavalin A, the expression level of mRNA is standardized with GDPDH mRNA, and the data represent the results of 8 experiments in each group.

Next, the cytokine production suppressing effects of cyclosporin A (CsA) and MES were compared using an inflammatory mouse model induced by concanavalin A. In the MES treatment group, the MES treatment was performed before and after administration of ConA, in the same manner as described above. CsA was administered 15 hours before and 40 minutes before the timing of the MES treatment in the MES treatment group to be compared, in an amount of 3.25 mg/kg. Kolliphor and PBS were used as controls for CsA and ConA, respectively. The total RNA was extracted from mouse spleen 4 hours after administration of ConA and the expression levels of IL-2, IL-6, IFN-γ and TNF-α were measured and compared by a quantitative RT-PCR method. The results are shown in FIG. 15. As a result, MES showed the same suppressive effect as CsA.

Example 8: Effect of MES on LPS-Induced Inflammatory Cytokine Production

Figure 16:
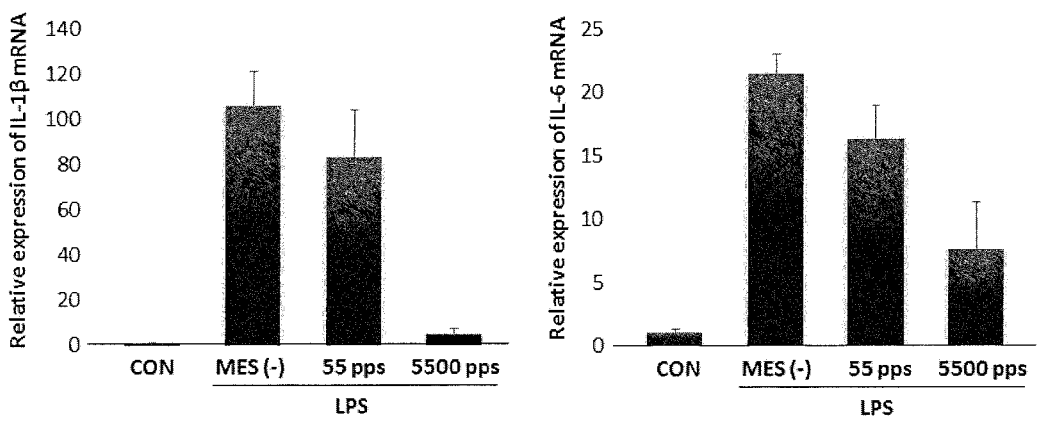
FIG. 16 is an illustration of exemplary results of the effect of a direct current (MES: MPES) on LPS-induced inflammatory cytokine production, using BV2 cells, a microglial cell line, the expression level of mRNA is standardized with GAPDH mRNA, and the data represent the results of 3 experiments in each group.

BV2 cells were seeded at a rate of 5×106 cells/dish in a 35 mm in dish, and the MES treatment was performed under conditions of 6 V, 37° C. for 10 minutes. The MES treatment was performed with MPES (6 V, 0.1 ms, 55 pps or 5500 pps) (Duty ratio=0.55% or 55%, respectively). Thirty minutes after the MES treatment, the cells were treated with LPS (100 ng/ml), cultured at 37° C. for 4 hours, then, the total RNA was collected and the expression levels of mRNA of IL-10 and IL-6 were measured and compared by a quantitative RT-PCR method. The results are shown in FIG. 16. MES 5500 pps significantly suppressed inflammatory cytokine production.

The above-described detailed description merely illustrates objects and subjects of the present disclosure, and does not limit the accompanying Claims. Without departing from the accompanying Claims, various modifications and alterations to the described embodiments will be apparent to those skilled in the art in view of the teachings herein.

INDUSTRIAL APPLICABILITY

The exemplary embodiments of the present disclosure can be useful for suppressing inflammation based on an immune action. The exemplary embodiments of the present disclosure can also safe be for living bodies. Furthermore, the exemplary embodiments of the present disclosure can be used in combination with existing immunosuppressive drugs, can reduce the amount of existing immunosuppressive drugs used and can suppress the occurrence of side effects, thus, the present disclosure is useful as a combinational therapy with existing immunosuppressive drugs.

EXPLANATION OF EXEMPLARY NUMERALS IN DRAWINGS

101: treatment apparatus
01: operation unit
02: current control unit
03: display unit
04: pad
05: electrode

EXEMPLARY CITATION LIST—INCORPORATED HEREIN BY REFERENCE

Patent Document(S)

Patent Document 1: Japanese Patent No. 5148254

Non-Patent Documents

Non-Patent Document 1: Morino et al., J. Pharmacol. Sci. 2008, vol. 108, pp. 222-226.
Non-Patent Document 2: Morino-Koga et al., J. Cell Ohysiol. 2012, vol. 228, pp. 439-446.
Non-Patent Document 3: Fukuda et al., J. Biol. CHem. 2013, vol. 288, pp. 16117-16226.
Non-Patent Document 4: Morino et al., PLos ONE 2008, vol. 3, e4068.
Non-Patent Document 5: Kondo et al., Diabetes 2012, vol. 61, pp. 8385-847.
Non-Patent Document 6: Ohba et al., J. Surg. Res. 2010, vol. 162, pp. 213-220.
Non-Patent Document 7: Koga et al., PLos ONE 2012, vol. 7, e43852.
Non-Patent Document 8: Kondo et al., E. BioMedicine 2014, vol. 1, pp. 80-89.

The invention claimed is:

1. An apparatus configured to pass a weak pulse direct current through a living body or a living tissue, comprising
   a power supply device; and
   a current control device configured to intermittently apply a direct current to the living body or the living tissue at a predetermined interval in response to a supply of electric power;
   wherein:
   the current control device includes a pulse width modulation control device,
   the pulse width modulation control device is configured to generate a pulse wave which is a rectangular wave in which a time indicating a peak value of a rising portion in one cycle of the pulse wave ("pulse duration") is at least 0.1 ms, the peak value is at least 1.0 V and at most 20 V, and a duty ratio of the pulse wave is at least 55%, and
   wherein the pulse width modulation control device applies the generated pulse wave to the living body or the living tissue.

2. The apparatus according to claim 1, wherein the apparatus is configured to pass the weak pulse direct current through the living body or the living tissue so as to suppress an inflammation thereof which is generated by a production of an inflammatory cytokine, and the inflammation suppression by the apparatus is based on a suppression of the production of the inflammatory cytokine.

3. The apparatus according to claim 1, wherein the apparatus is configured to pass the weak pulse direct current through the living body or the living tissue so as to suppress an inflammation thereof which is generated by a production of at least one inflammatory cytokine selected from the group consisting of IL-2, IL-6, TNF-α and INF-γ, and the inflammation suppression by the apparatus is based on a suppression of the production of the inflammatory cytokine.

4. The apparatus according to claim 3, wherein the inflammatory cytokine is IL-2.

5. The apparatus according to claim 1, wherein the intermittent interval of the direct current is at least 55 pps, and wherein the pulse duration is at least 10 ms.

6. The apparatus according to claim 1, wherein the intermittent interval of the direct current is at least 550 pps, and wherein the pulse duration is at least 1 ms.

7. The apparatus according to claim 1, wherein the intermittent interval of the direct current is at least 5500 pps.

8. The apparatus according to claim 1, further comprising a plurality of conductive pads configured to be attached to surfaces of different sites of the living body or the living tissue, wherein the current control device is configured to generate the weak direct current intermittently between at least two of the pads during operation when the pads are attached to the living body or the living tissue.

9. The apparatus according to claim 1, wherein the apparatus is configured to pass the weak pulse direct current through the living body or the living tissue so as to suppress an inflammation thereof that is based on a disease selected from the group consisting of systemic autoimmune diseases and organ-specific autoimmune diseases.

10. The apparatus according to claim 1, wherein the apparatus is configured to pass the weak pulse direct current through the living body or the living tissue so as to treat an inflammation thereof based on a disease selected from the group consisting of systemic autoimmune diseases and organ-specific autoimmune diseases.

11. The apparatus according to claim 1, wherein the apparatus is configured to pass the weak pulse direct current through the living body or the living tissue in a patient receiving an immunosuppressive drug.

12. The apparatus according to claim 1, wherein the direct current is provided to and through the living body or the living tissue in a direct current state.

13. The apparatus according to claim 1, wherein the direct current is provided to the living body or the living tissue through a pad pasted to or on the living body or the living tissue.

14. A method for treating an inflammation in a living body or a living tissue, comprising:
providing a weak pulsed direct current to and through the living body or the living tissue thereby suppressing the inflammation in the living body or the living tissue, wherein a shape of a pulse wave of input power being provided is rectangle, a time indicating a peak value of a rising portion in one cycle of the pulse wave ("pulse duration") is at least 0.1 ms, the peak value is at least 1.0 V and at most 20 V, and a duty ratio of the pulse wave is at least 55%.

15. The method according to claim 14, wherein the inflammation is an inflammation generated by a production of an inflammatory cytokine, and the inflammation suppression is based on a suppression of the production of the inflammatory cytokine.

16. The method according to claim 14, wherein the inflammation is an inflammation generated by a production of at least one inflammatory cytokine selected from the group consisting of IL-2, IL-6, TNF-α and INF-γ, and the inflammation suppression is based on a suppression of the production of the inflammatory cytokine.

17. The method according to claim 16, wherein the inflammatory cytokine is IL-2.

18. The method according to claim 14, further comprising intermittently applying a direct current at a predetermined interval in response to a supply of electric power, wherein the intermittent interval of the direct current is at least 55 pps and the pulse duration is at least 10 ms.

19. The method according to claim 14, further comprising intermittently applying a direct current at a predetermined interval in response to a supply of electric power, wherein the intermittent interval of the direct current is at least 550 pps, and the pulse duration is at least 1 ms.

20. The method according to claim 14, further comprising intermittently applying a direct current at a predetermined interval in response to a supply of electric power, wherein the intermittent interval of the direct current is at least 5500 pps.

21. The method according to claim 14, wherein the inflammation is based on a disease selected from the group consisting of systemic autoimmune diseases and organ-specific autoimmune diseases.

22. The method according to claim 14, wherein the method treats the inflammation in a patient receiving an immunosuppressive drug.

23. The method according to claim 14, wherein the pulse direct current is provided to and through the living body or the living tissue in a direct current state.

24. The method according to claim 14, wherein the weak pulsed direct current is provided to and through the living body or the living tissue through a pad pasted to or on the living body or the living tissue.

* * * * *

UNITED STATES PATENT AND TRADEMARK OFFICE
CERTIFICATE OF CORRECTION

PATENT NO. : 11,135,425 B2
APPLICATION NO. : 15/768253
DATED : October 5, 2021
INVENTOR(S) : Hirofumi Kai et al.

Page 1 of 1

It is certified that error appears in the above-identified patent and that said Letters Patent is hereby corrected as shown below:

On the Title Page

Item (73) Assignee should read: NATIONAL UNIVERSITY CORPORATION KUMAMOTO UNIVERSITY, Kumamoto (JP); and TERUMO KABUSHIKI KASISHA, Tokyo (JP)

Signed and Sealed this
Eleventh Day of March, 2025

Coke Morgan Stewart
*Acting Director of the United States Patent and Trademark Office*